United States Patent [19]
Kanda et al.

[11] Patent Number: 5,397,537
[45] Date of Patent: Mar. 14, 1995

[54] TEST INSTRUMENT

[75] Inventors: Zensho Kanda; Katsuhiko Miyaguchi; Masufumi Koike; Tsuyoshi Hayakawa; Naoki Morikawa, all of Yamanashi, Japan

[73] Assignee: Terumo Kabushiki Kaisha, Tokyo, Japan

[21] Appl. No.: 162,976

[22] Filed: Dec. 8, 1993

Related U.S. Application Data

[63] Continuation of Ser. No. 887,649, May 26, 1992, abandoned, which is a continuation of Ser. No. 578,599, Sep. 7, 1990, abandoned.

[30] Foreign Application Priority Data

Sep. 8, 1989 [JP] Japan .................................. 1-231551
Sep. 8, 1989 [JP] Japan .................................. 1-231553

[51] Int. Cl.$^6$ ............................................ G01N 21/00
[52] U.S. Cl. ............................ 422/56; 422/57; 422/58; 435/16; 436/168; 436/169
[58] Field of Search ...................... 422/56, 57, 58; 436/168, 169; 435/16

[56] References Cited

U.S. PATENT DOCUMENTS

| | | | |
|---|---|---|---|
| 3,718,439 | 2/1973 | Rosse et al. | 422/67 |
| 3,791,933 | 2/1974 | Moyer et al. | 422/56 |
| 4,251,159 | 2/1981 | White | 422/58 |
| 4,292,272 | 9/1981 | Kitajima et al. | 422/56 |
| 4,387,990 | 6/1983 | Yazawa et al. | 356/244 |
| 4,631,174 | 12/1986 | Kondo | 422/56 |
| 4,668,472 | 5/1987 | Sakamoto et al. | 422/56 |
| 4,717,656 | 1/1988 | Swanljung | 422/56 |
| 4,738,823 | 4/1988 | Engelmann | 422/56 |
| 4,912,034 | 3/1990 | Kalra et al. | 422/58 |
| 4,952,373 | 8/1990 | Sugarman et al. | 422/58 |

FOREIGN PATENT DOCUMENTS

| | | |
|---|---|---|
| 0325398 | 7/1989 | European Pat. Off. |
| 32 22 707 | 12/1982 | Germany |
| 34 42 820 | 6/1985 | Germany |
| 61-61347 | 12/1986 | Japan |
| 63-334198 | 7/1990 | Japan |

OTHER PUBLICATIONS

Norbert W. Tietz et al, "Textbook of Clinical Chemistry," W. B. Saunders Co., pp. 669–671 (1986).
Kodak Ektachem Clinical Chemistry Slides, "Alanine Aminotransferase ALT" (1986).
Kodak Ektachem Clinical Chemistry Slides, "Aspartate Aminotransferase AST" (1986).
E. Knoll et al., "The Determination of Calcium, Glucose, Urea and Uric Acid Using the Koda Ektachem Multilayer Film Technology: An Evaluation", *J. Clin. Chem. Clin. Biochem.*, vol. 20, 1982, pp. 491–498.

*Primary Examiner*—W. Gary Jones
*Assistant Examiner*—Laura E. Edwards
*Attorney, Agent, or Firm*—Burns, Doane, Swecker & Mathis

[57] ABSTRACT

A test instrument for uniformly spreading a collected specimen on a reagent layer has a first opening for collecting the specimen, a specimen spreading layer having an upper surface a portion of which is exposed to the first opening, the reagent layer provided so that an upper surface thereof is in contact with the lower surface of the specimen spreading layer, and a support layer provided on a lower surface of the reagent layer. Even if the specimen does not attached itself in a uniform distribution over the large area of the first opening, it will be evenly distributed at the second opening, the opening area of which is smaller than that of the first opening at which measurement is performed. When an absorbing layer provided in the proximity of the edge portion of the first opening is supplied with an excess amount of the specimen, a direct path to the absorbing layer is blocked by the inner peripheral region of the first opening so that the absorbing layer is soaked via the spreading layer. Consequently, the specimen is distributed on the reagent layer uniformly and at a fixed concentration irrespective of the amount thereof.

35 Claims, 7 Drawing Sheets

TEST INSTRUMENT

This application is a continuation of application Ser. No. 07/887,649, filed May 26, 1992, now abandoned, which is a continuation of application Ser. No. 07/578,599, filed Sep. 7, 1990, now abandoned.

BACKGROUND OF THE INVENTION

1. Field of the Invention

This invention relates to a test instrument and, more particularly, to a test instrument in which, by way of example, the color reaction of various sampled specimens is measured automatically by a measuring device.

2. Description of the Prior Art

A multi-layered analytical sheet for liquid-sample analysis, in which quantitative measurement of a specific component of a specimen is performed in a simple manner, is disclosed in the specification of Japanese Patent Publication (KOKOKU) No. 61-61347. This multi-layered analytical sheet for liquid-sample analysis is disadvantageous in that the reaction time is long owing to structural limitations.

In view of this drawback, the applicant has proposed, in Japanese Patent Application No. 63-334198 entitled "Test Instrument", a test instrument exhibiting a shortened reaction time. In order to analyze a component contained in a specimen, this test instrument includes a light-transmissive support member on one surface of which is provided with a reagent layer and a spreading layer for uniformly spreading the specimen. The instrument is integrated by the pressing action of a holding member in such a manner that the spreading layer is situated on the outer side.

With the "Test Instrument" proposed by the applicant, the time needed for a sampled specimen to reach and soak the reagent layer is shortened and the permeability of a gas such as oxygen necessary for a color reaction is enhanced, thereby hastening the rate of the color reaction. On the other hand, the test instrument may be inserted into an insertion port of a test device and used together with the test device, which is adapted to measure the elapsed time of the color reaction.

Figure 9:
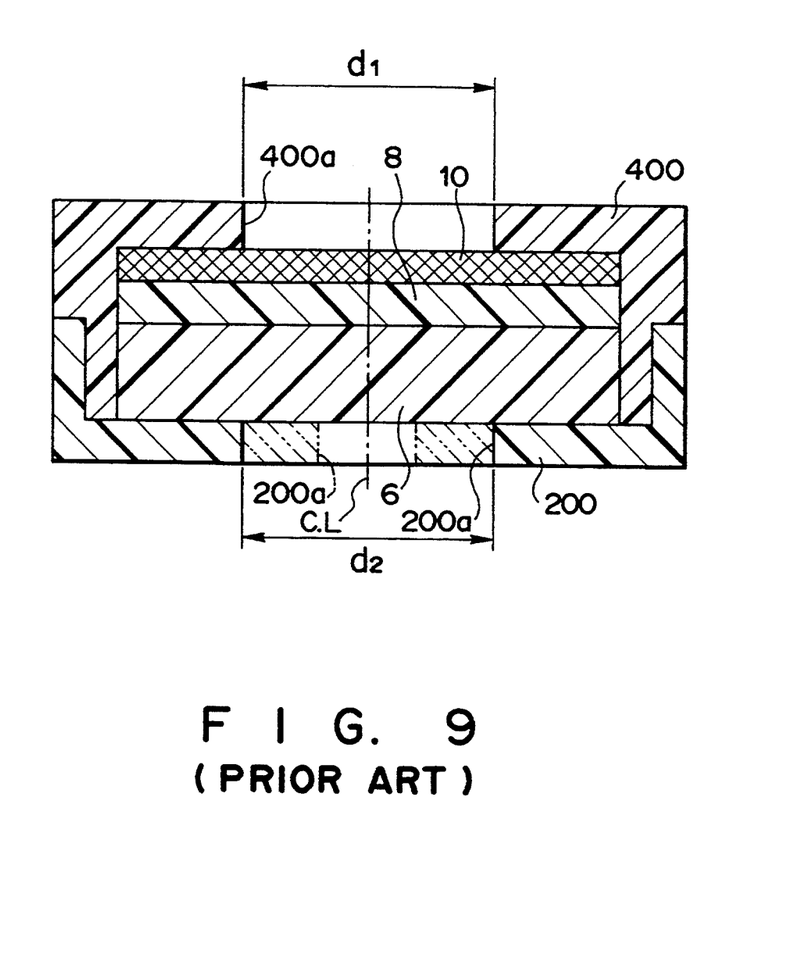
FIG. 9 is a sectional view showing a test instrument previously proposed by the applicant.

FIG. 9 is a sectional view of the test instrument proposed by the applicant. This sectional view is broken away along a plane passing through the center of a circular opening in the instrument. As shown in FIG. 9, the test instrument, has a main body 200 in which an opening 200a of diameter $d_2$ is formed. A cover 400 is integrally provided on the main body 200 as by bonding. The cover 400 is provided with an opening 400a of radius $d_1$, which is approximately the same as diameter $d_2$. The central axis of the cover 400 is made to coincide with a center line CL of the opening 200a in main body 200.

A light-transmissive layer 6 comprising a transparent resin material has a portion of its lower side exposed to the outside via the opening 200a. A reagent layer 8 for undergoing a color reaction with a specimen is provided on the upper surface of the light-transmissive layer 6. A liquid spreading layer 10 is disposed on the reagent layer 8, and a portion of the upper surface of the liquid spreading layer 10 is exposed to the outside via the opening 400a. The lower surface of the liquid spreading layer 10 is in contact with the reagent layer 8.

In accordance with this arrangement, a sampled specimen is developed by the liquid spreading layer 10 via the opening 400a, after which the specimen soaks the reagent layer 8 to cause a color reaction. This color reaction is measured by optical measuring means to obtain a measurement value. In order to perform this measurement, the opening 200a in the main body 200 is irradiated with light from a light-emitting element, the amount of reflected light, which varies in approximate proportion to the color reaction, is detected by a light-receiving element, and a change in the color reaction with time is measured. This method can be used to measure blood-sugar value, by way of example.

In this "Test Instrument" proposed by the applicant, the diameter of the opening 200a to the transparent light-transmissive layer 6 and the diameter of the opening 400a to the liquid spreading layer 10 are substantially the same, as mentioned above. Therefore, it is required that the specimen which has reacted with the reagent layer 8 be distributed uniformly over the entire area of the opening 200a to the light-transmissive layer 6 by spreading the specimen evenly over the entire area of the opening 400a to the liquid spreading layer 10. However, if too much of the specimen attaches itself at this time, the specimen cannot be distributed uniformly and the excess specimen, which has no place else to go, will drip from the instrument.

In addition, though it is necessary for the specimen which has reacted with the reagent layer 8 to be distributed uniformly over the entire area of the opening 200a to the light-transmissive layer 6, it is very difficult to uniformly distribute the specimen over such a wide area in this manner.

SUMMARY OF THE INVENTION

Accordingly, an object of the present invention is to provide a test instrument in which, even if an excess amount of a sampled specimen attaches itself to the instrument, the specimen can be distributed on the reagent layer uniformly and at a constant concentration, and in which excess specimen will not drip from the instrument.

Another object of the invention is to provide a test instrument in which, when an excess amount of a specimen attaches itself to the instrument, the specimen is kept from contacting an absorbing layer prior to the spreading layer to suppress excessive absorption by the absorbing layer, whereby absorption can be controlled so as to enable a suitable amount of development.

Still another object of the invention is to provide a test instrument in which a specimen is evenly distributed on an opening, at which measurement is to take place, even if the specimen is not uniformly distributed over a wide area.

According to the present invention, the foregoing objects are attained by providing a test instrument on which a specimen is spread for being measured by a measuring device and having a first opening for passing said specimen, a specimen spreading layer having a portion of which is exposed to said first opening, a reagent layer in contact with said spreading layer, provided on a opposite side of said first opening, a support member in contact with said reagent layer, and provided on a opposite side of said first opening, and a second opening, at which measurement is performed by said measuring device, situated on an opposite side of said first opening, wherein said second opening has an opening area set to be smaller than an opening area of said first opening, and a uniformly affixed portion of said specimen is exposed to said second opening. The test instrument is further provided with an absorbing layer for absorbing the collected specimen, an excess of amount of which has collected in the vicinity of the edge portion of the first opening. Therefore, even if an excess amount of the specimen is supplied to the first opening, the specimen will be absorbed by the absorbing layer so that the specimen will be distributed on the reagent layer uniformly and at a fixed concentration.

The inner peripheral region of the first opening in a cover for forming the first opening is formed to have a curved or planar surface. By being pressed against the specimen spreading layer, the time needed for the supplied specimen to reach the absorbing layer is prolonged and a suitable amount of the specimen is caused to soak the spreading layer and the reagent layer. While this is taking place, only surplus specimen soaks the absorbing layer.

The specimen is evenly distributed on the second opening, at which measurement takes place, even if the specimen is not uniformly distributed over the wide area of the first opening.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENT

An embodiment of the present invention will now be described in detail with reference to the accompanying drawings.

Figure 1:
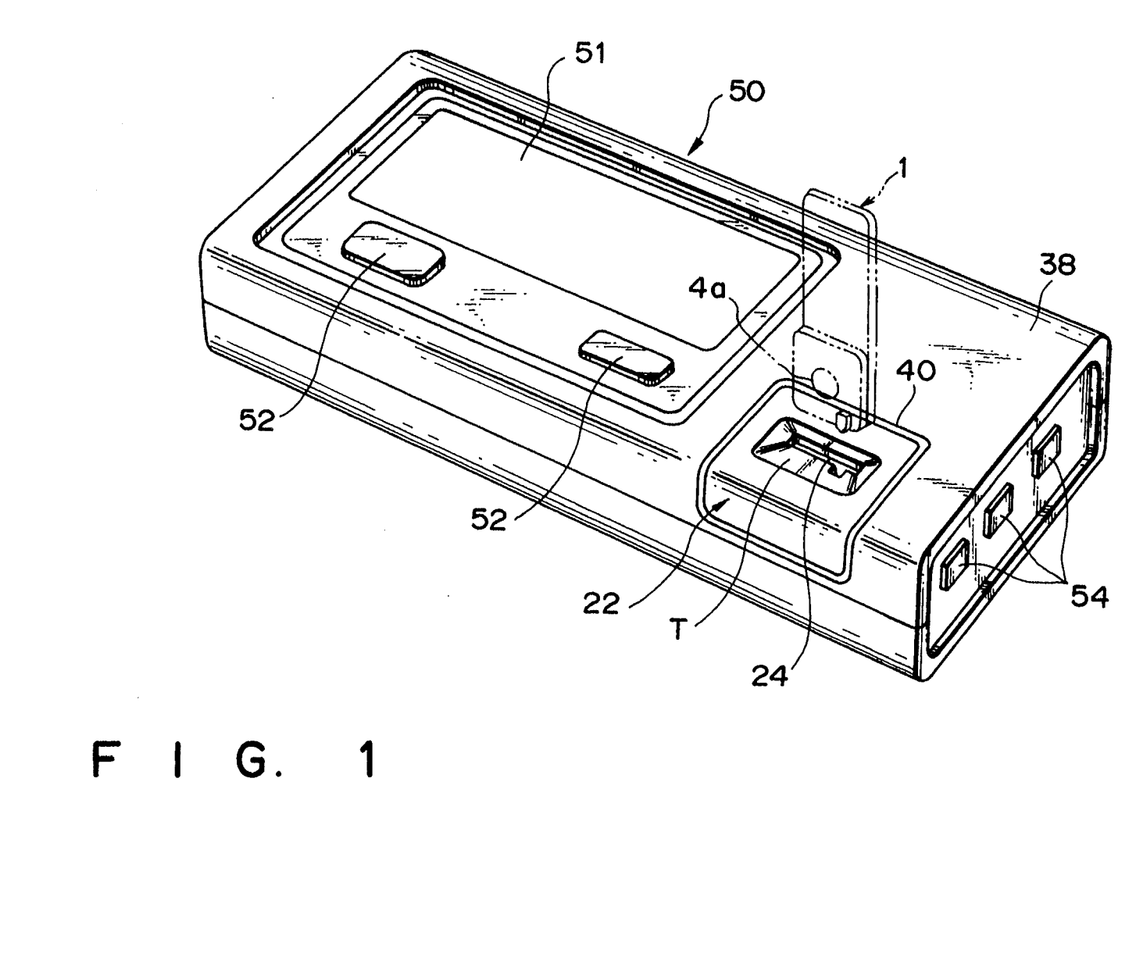
FIG. 1 is an external perspective view of a measuring device related to automatic measurement using a test instrument embodying the present invention.

With reference to FIG. 1, there is shown a measuring device 50 adapted for measuring blood-sugar value. The measuring device 50 is provided with an insertion hole 24 into which a test instrument 1, indicated by the phantom lines, is inserted.

In FIG. 1, the measuring device 50 is formed to have a cover body 38 as its outer surface. The left-hand side of the upper surface of cover body 38 is provided with a display panel comprising a liquid-crystal cell or the like. Provided immediately below the display panel 51 are a power-supply switch 52 for turning a power supply on and off, and a memory call button 53 which, by being pressed, calls the date of the last measurement and the blood-sugar value measured on that date and causes this data and blood-sugar value to be displayed on the display panel 51. The right-hand end face of the measuring device 50 is provided with a total of three operating switches 54. These switches are used to set and change the date of a measurement, to store and set the results of measurement, etc.

An auxiliary cover body 22 is detachably provided on the top side of the right-hand portion of the measuring device 50. The auxiliary cover 22 makes it easy to insert the test instrument 1 by being formed to include a tapered portion T which starts from the edge of the insertion hole 24. An opening 40 in which the auxiliary cover 22 is fixed is formed in the cover 38 and extends across part of its front side.

There are two reasons for thus detachably fixing the auxiliary cover 22 to the cover 38. One is so that the auxiliary cover 22 can be detached and washed if the insertion hole 24 of the auxiliary cover 22 should become contaminated with blood or dust. The other reason is to make it possible to gain access to a light-transmissive body 32, described below, in order to clean the surface of the light-transmissive body 32 using a cotton swab or the like.

As shown in FIG. 1, the test instrument 1 is inserted into the insertion hole 24 from above with an opening 4a thereof facing forward. Since measurement would be impossible if the test instrument 1 were inserted backwards, means (described below) for preventing such backward insertion is provided.

Figure 2:
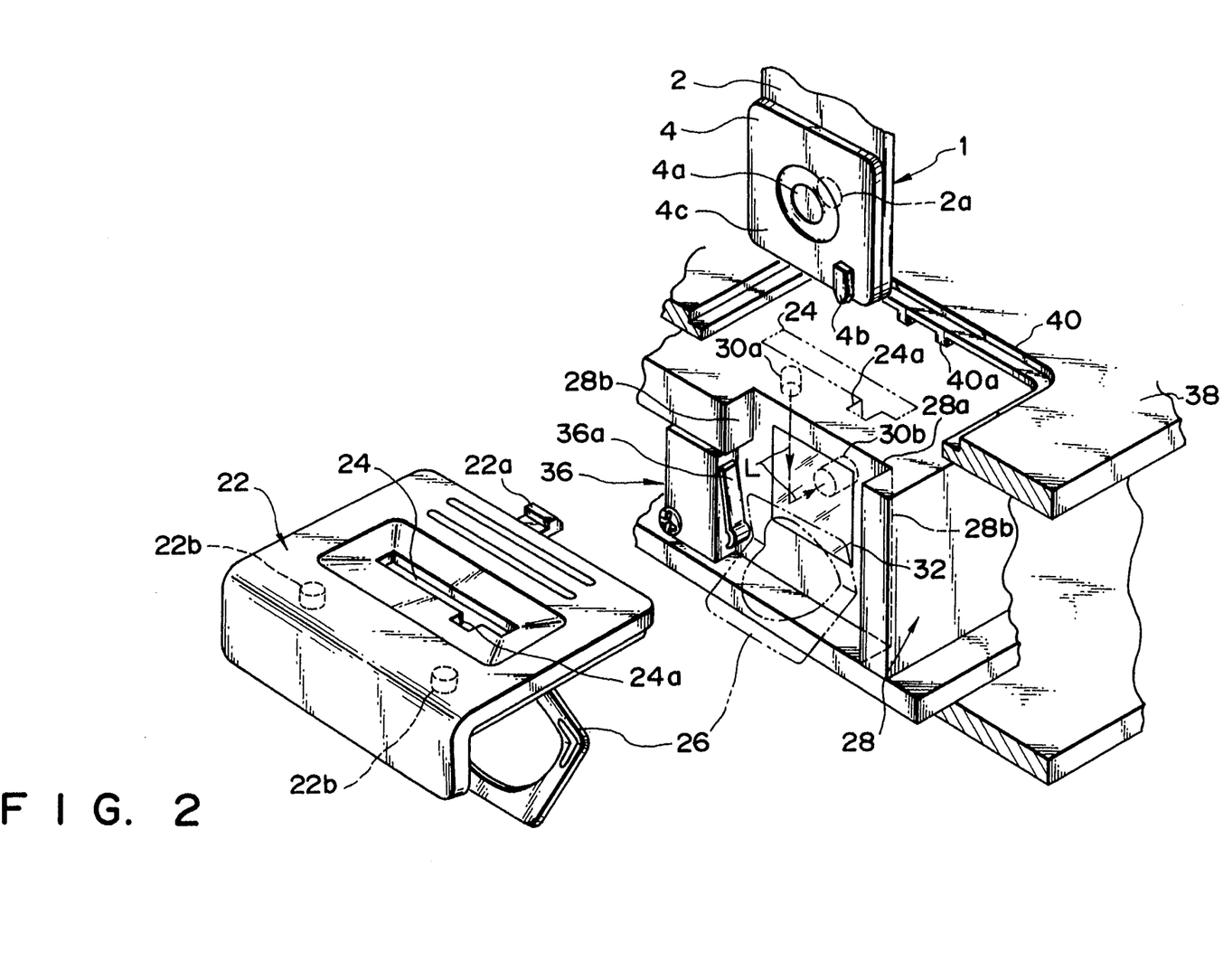
FIG. 2 is an external perspective view of showing the measurement portion of the measuring device shown in FIG. 1.

FIG. 2, which is an external perspective view of the measuring section of the measuring device, shows the upper and lower portions of the cover 38 broken away in order to make it easier to see the interior of the measuring section in which the test instrument 1 is inserted. The auxiliary cover 22 is illustrated in a state detached from the opening 40 in cover 38. The dashed lines in FIG. 2 indicate the insertion hole 24 when the auxiliary cover 22 has been attached to the cover 38.

Similarly indicated by solid and dashed lines is a spring 26 one end of which is fixedly supported by studs 22b formed on the bottom surface of the auxiliary cover 22 and indicated by the dashed lines. When the auxiliary cover 22 is attached to the cover 38, as illustrated in FIG. 1, so that the spring 26 is fixed at the position indicated by the dashed lines, the outer surface 4c of the test instrument 1 is urged by the abutting distal end portion of the spring 26. As a result, when the test instrument 1 is inserted from above and set at a prescribed measuring position, the resilient biasing force of the spring 26 prevents the instrument 1 from moving from the measuring position.

After the freely detachable auxiliary cover 22 has been attached to the cover 38, it must resist a predetermined external force. To this end, a portion of the opening 40 of cover body 38 is formed to have a locking portion 40a, and a part of the auxiliary cover 22 is formed to have a male locking member 22 which engages with the locking portion 40a, as illustrated.

A portion of the inner peripheral surface of insertion hole 24 is formed to have a cut-out 24a. The cut-out 24 is shaped and positioned to mate with a projection 4b formed on the lower right-hand edge of the outer surface 4c of test instrument 1. As a result, the arrangement is such that the test instrument 1 can be inserted into the insertion hole 24 from above only if the opening 4a thereof is faced toward the front. This prevents backward insertion of the test instrument 1.

A sensor 28 is a molded member comprising a light-shielding material integrally provided on a board on which electronic parts are mounted. As shown in FIG. 2, the sensor 28 has a groove the transverse cross section of which has a U-shaped configuration that allows the test instrument 1 to be inserted from above. The groove includes two side portions 28b and an abutting-contact portion 28a. A microswitch 36 having an actuator 36a is fixedly secured to the lower half portion of one of the two side portions 28b. Inserting the test instrument 1 moves the actuator 36a to the ON state, thereby starting measurement automatically.

Electronic components provided within the sensor 28 include a light-emitting element 30a and a light-receiving element 30b which respectively emit and receive light of a predetermined wavelength along an optical path L indicated by the dashed line in FIG. 2. Light emitted by the light-emitting element 30a irradiates a light-transmissive layer (described below) provided at an opening 2a of the test instrument 1. The amount of light reflected from a reagent layer, which is disposed on the backside of the irradiated light-transmissive layer, is sensed by the light-receiving element 30b. This is the basic operating principle of the sensor 28. The light-transmissive body 32, which consists of glass or the like, is provided at a predetermined position of the sensor body 28 opposing the opening 2a of the test instrument 1.

Figure 3:
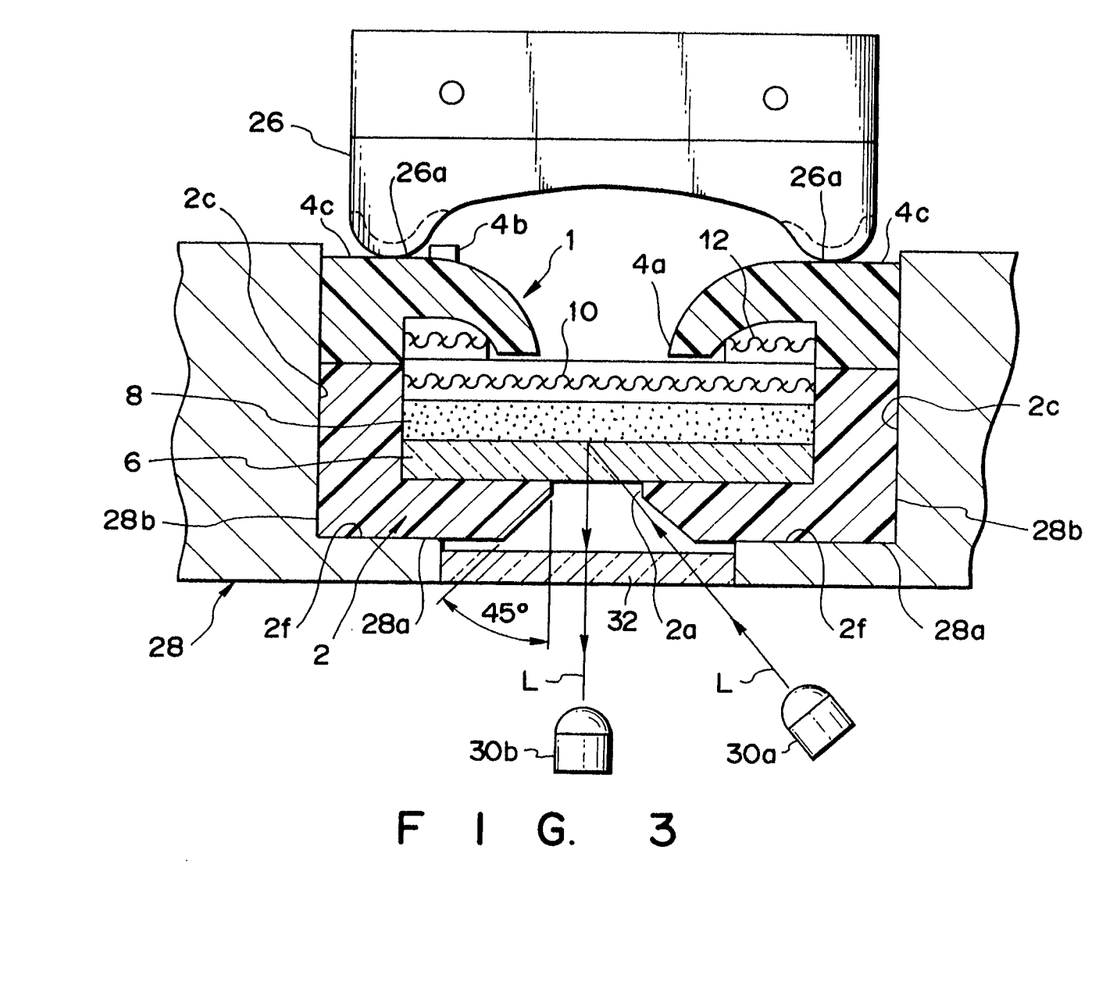
FIG. 3 is a transverse sectional view showing the measurement portion of FIG. 2.

FIG. 3, which is a transverse sectional view of the measuring section, shows the manner in which the light emitted by the light-emitting element 30a travels along the optical path L and finally impinges upon the light-receiving element 30b. As shown in FIG. 3, the test instrument 1 has two side portions 2c and an external surface 2f which come into abutting contact with the two side portions 28b and abutting-contact portion 28a, respectively, forming the groove of the sensor 28. The test instrument 1 is held in the position illustrated by having its outer surface 4c urged by a pair of arcuate contact portions 26a formed on the spring 26. With the test instrument held in this state, light from the light-emitting element 30a passes through the light-transmissive body 32, is reflected at the reagent layer 8 and then again passes through the light-transmissive body 32. The light travels along the optical path L.

Since the optical path L is thus made to reach the reagent layer 8, the edge portion of the opening 2a of test instrument 1 is chamfered to an annular shape at a predetermined angle (e.g., 45°), as illustrated. Thus, the arrangement is such that the edge portion of opening 2a will not obstruct the optical path L. At the same time, it is arranged so that the allowable range of the angle at which the light-emitting element 30a is mounted with respect to the light-receiving element 30b can be set to a large value.

The edge portion of the opening 2a is not limited to the angle of 45° illustrated, and it is not necessary for the entire circumference thereof to be chamfered. In other words, it will suffice if a portion of the edge of opening 2a is so chamfered as not to obstruct the optical path L.

Figure 4:
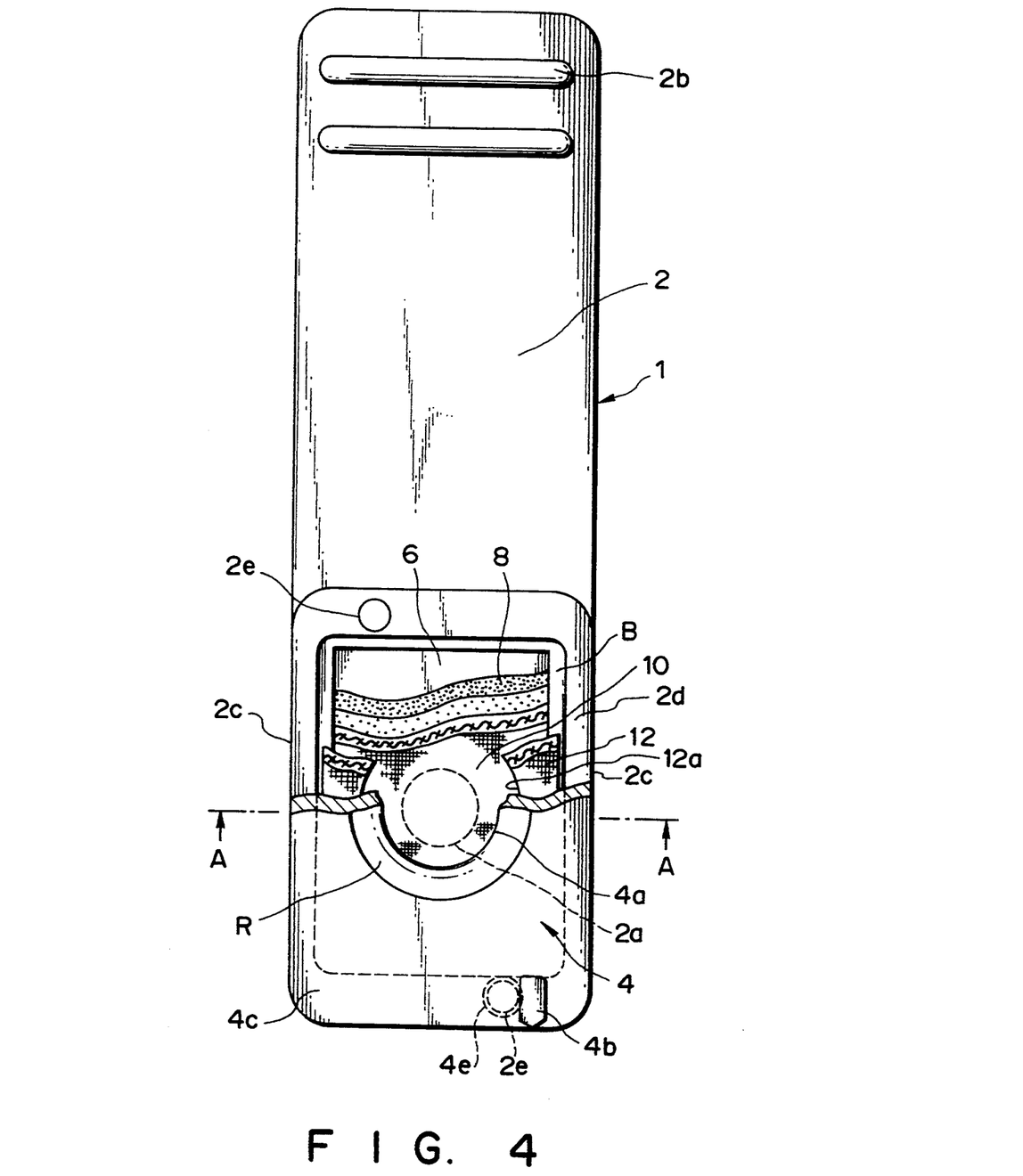
FIG. 4 is a front view, partially broken away, showing the test instrument of the embodiment.

FIG. 4 is a front view, partially broken away, showing the test instrument 1. The test instrument 1 has a main body 2 serving as a base portion and comprising a resin material capable of being injection molded and mass-produced in stable fashion. The main body 2 has an upper-half portion the surface of which is formed to include two ribs 2b capable of being felt by the fingers of the patient when the instrument is grasped, and a lower-half portion formed to include a rectangular junction portion 2d centered on the opening 2a (indicated by the dashed line) whose edge is formed to have the aforementioned chamfered portion. A box B is formed on the lower-half portion of the main body 2.

Set inside the box B are, in order from bottom to top, a light-transmissive layer 6 on one surface of which is exposed at the opening 2a, a reagent layer 8, which is applied to the light-transmissive layer 6, for reacting with a specimen such as blood, a liquid spreading layer 10 made of cloth for uniformly applying a sample on the reagent layer 8, and liquid-absorbing layer 12 for absorbing the sample supplied in excess to the liquid spreading layer 10. The light transmissive layer 6 is one portion of support member.

The liquid-absorbing layer 12 is provided with an opening 12a having a diameter larger than that of the opening 4a in cover 4. The liquid-absorbing layer 12 can be installed on the inner side of a radius portion R in which the radius up to the opening 4a of the cover 4 is about 2.8 mm. A member exhibiting an excellent water absorption property, such as filter paper or cotton, is used as the liquid-absorbing layer 12.

The cover 4 having the opening 4a provided substantially at its center is positioned with respect to a guide hole 2e, which is formed in the junction portion 2d of main body 2, while being guided by a stud 4e (indicated by the dashed line) provided on the cover 4. Thereafter, the junction portion 2d of main body 2 and a junction portion 4d (described below) of the cover 4 are bonded together as by ultrasonic welding or adhesive to complete the fabrication of the test instrument 1.

Figure 5:
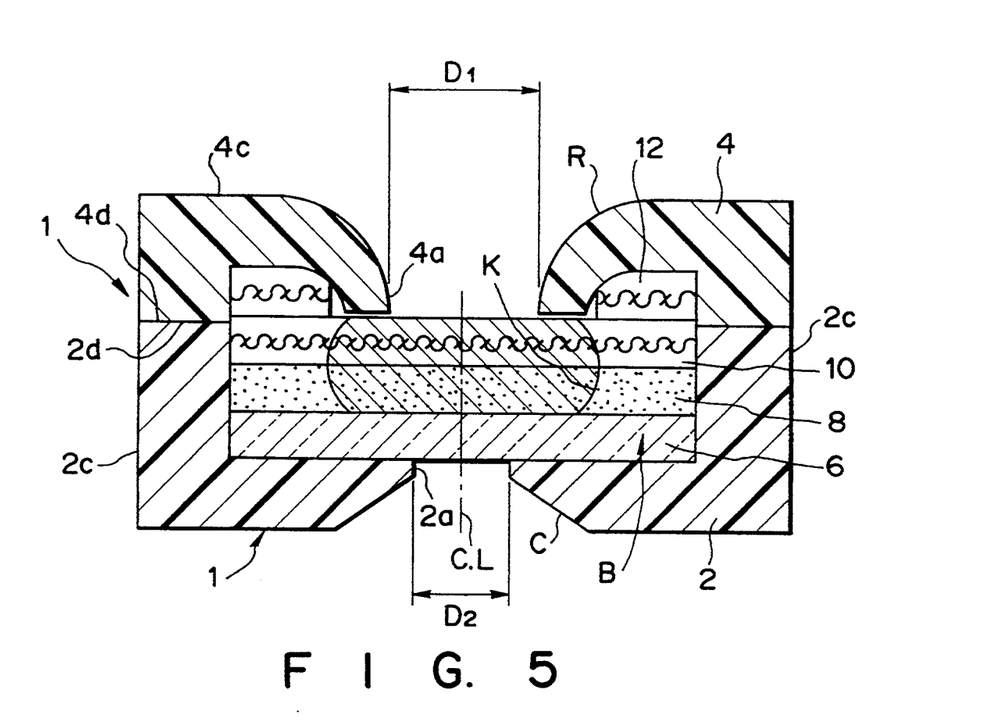
FIG. 5 is a sectional view broken away along a plane passing through the center of an opening in the test instrument

FIG. 5 is a transverse sectional view of the test instrument 1. The cover 4 of test instrument 1 is provided with the circular opening 4a, of diameter $D_1$, constituting a first opening, and the main body 2 is provided with the circular opening 2a, of diameter $D_2$ that is approximately half of diameter $D_1$, constituting a second opening. The opening 2a has a central axis common with the center line C.L of the opening 4a in cover 4. A comparatively hard resin such as polycarbonate resin is used as the cover 4. The light-transmissive layer 6, which comprises a transparent resin material or the like, has a lower surface a portion of which is exposed to the outside at the opening 2a. The reagent layer 8 for undergoing a color reaction with a specimen is provided on the upper surface of the light-transmissive layer 6, and the liquid spreading layer 10 is laid upon the reagent layer 8. A portion of the upper surface of the liquid spreading layer 10 is exposed to the outside via the opening 4a. The lower surface of the liquid spreading layer 10 is in contact with the reagent layer 8.

The absorbing operation of the test instrument 1 having the aforementioned construction will now be described. When a proper amount of a specimen K (indicated by the slanted lines in FIG. 5) is supplied, the specimen K is developed on the liquid spreading layer 10 via the opening 4a, after which the specimen soaks the reagent layer 8 and causes a color reaction. A measurement value is obtained by measuring the color reaction using the optical measuring means. To this end, the opening 2a in main body 2 is irradiated with light from the light-emitting element, and the amount of reflected light, which varies approximately in proportion to the color reaction, is detected by the light-receiving element. By way of example, a change in the color reaction with the passage of time can be measured to perform measurement of blood-sugar value.

Figure 6:
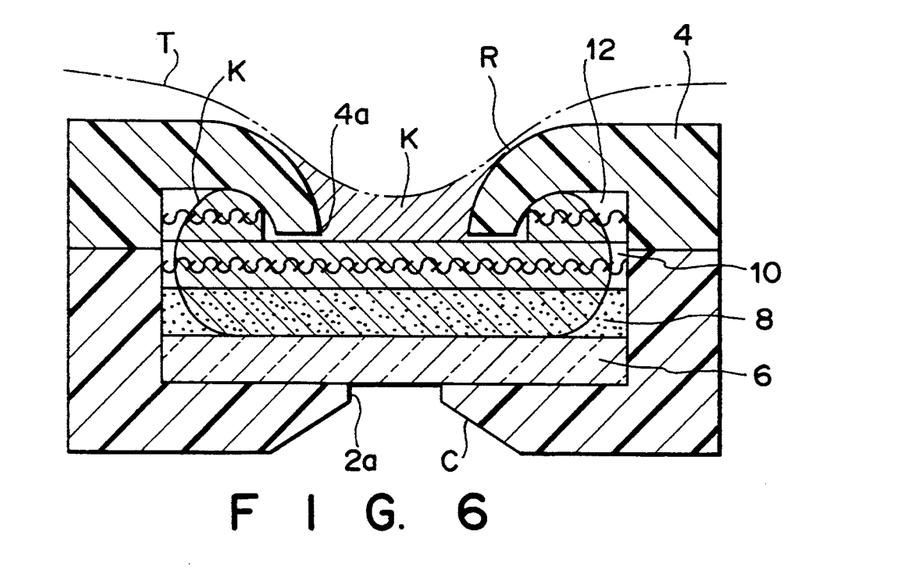
FIG. 6 is a sectional view showing the manner in which a specimen is supplied in excess.

FIG. 6 is a sectional view showing the manner in which an excess amount of the specimen K attaches itself to the instrument. More specifically, FIG. 6 illustrates the manner in which an excess amount of the specimen K, indicated by the slanted lines, is supplied from a finger tip T, denoted by the two-dot chain line. As shown in FIG. 6, the specimen K, which is blood extracted from the finger tip T, soaks the liquid spreading layer 10 from the opening 4a and then soaks the reagent layer 8. When the specimen K is collected from the finger, the finger tip T deformed as illustrated along the radius portion R of opening 4a. As a result, though the distance between the specimen K and liquid-absorbing layer 12 is reduced, the direct path to the absorbing layer is blocked by the R portion of opening 4a so that the absorbing layer 12 is soaked via the liquid spreading layer 10. Consequently, the specimen is split between the reagent layer 8 and the absorbing layer 12 to supply the reagent layer 8 a soaking amount of the specimen. As a result, the specimen is quantitatively measured out irrespective of the amount thereof and surplus specimen is absorbed by the liquid-absorbing layer 12.

Figure 7:
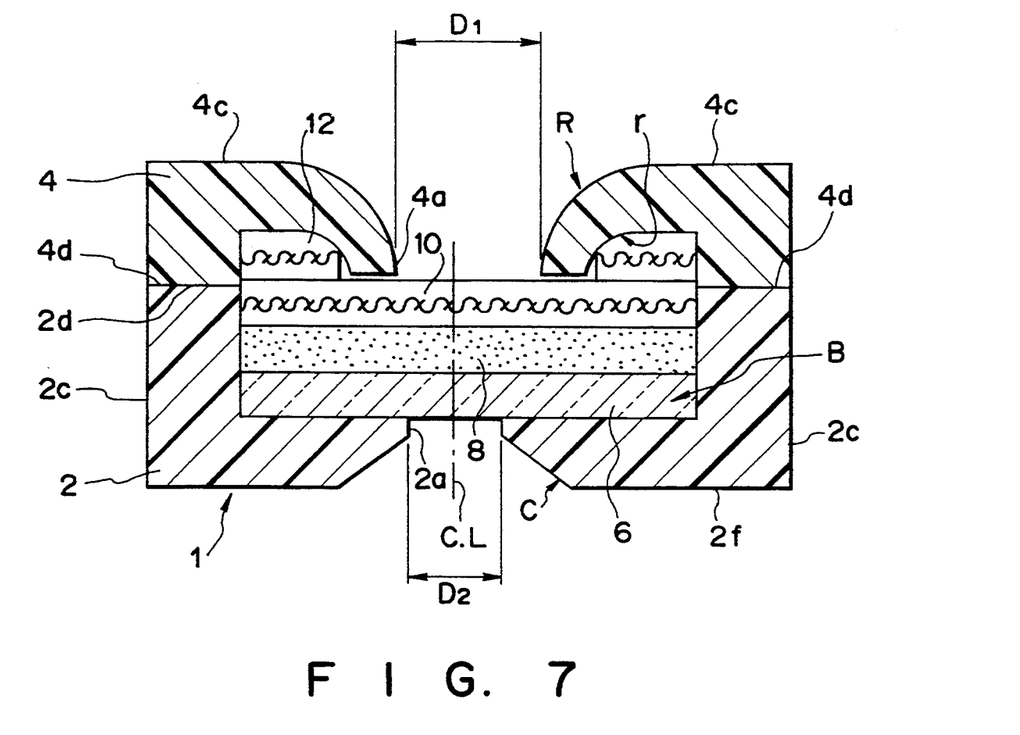
FIG. 7 is a sectional view broken away along a plane passing through the center of an opening in the test instrument.

FIG. 7 is a sectional view broken away along a plane passing through the center of the opening of the test instrument and shows the state of the test instrument before it is soaked by the specimen K. Portions identical with those shown in FIG. 6 are designated by like reference characters.

Figure 8:
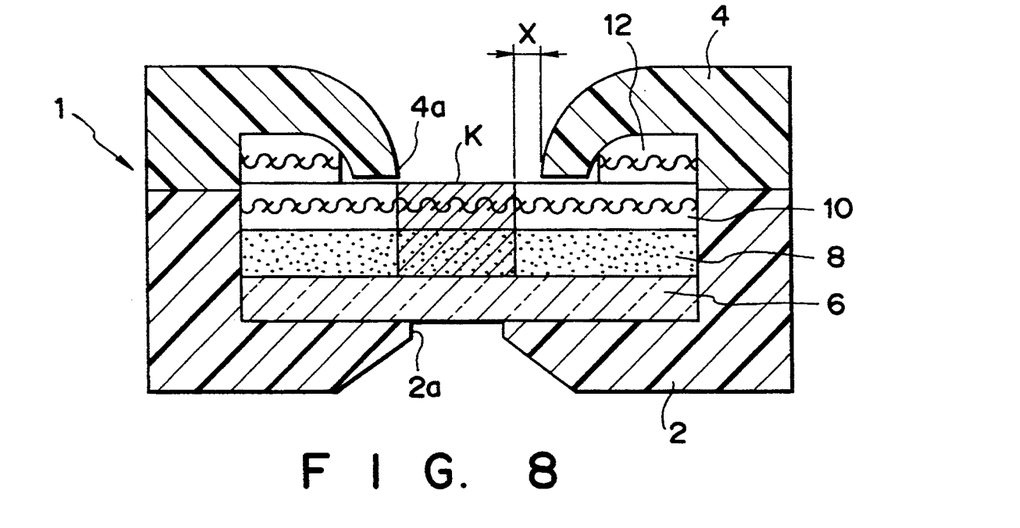
FIG. 8 is a sectional view showing the manner in which a specimen is supplied.

FIG. 8 is a sectional view showing the manner in which the specimen K attaches itself. As shown in FIG. 8, the specimen K of blood extracted from the finger tip or the like soaks the liquid spreading layer 10 from the opening 4a and then soaks the reagent layer 8. The fact that the opening 2a is smaller than the opening 4a means that a portion X free of the specimen K, which may exist at the opening 4a when the specimen K is collected, as shown in FIG. 8, will not be exposed to the opening 2a. In other words, if it is so arranged that the specimen K attaches itself with the center of the opening 4a serving as a reference, then a portion evenly coated with the specimen K will appear with certainty at the opening 2a where measurement is performed.

The method in which the test instrument 1 thus constructed is used will now be described.

First, the power-supply switch is closed so that a display indicating the start of measurement will appear on the display panel 51. The test instrument 1 which has collected a specimen sample is then inserted into the insertion hole 24. As a result, the microswitch 36 attached to the sensor 28 in FIG. 2 is contacted by one of the two side surfaces 2c of test instrument 1, whereby the switch is closed. Immediately after this occurs, the elapsed time of the color reaction that takes place in the reagent layer 8 soaked with the specimen is measured by the light-emitting element 30 and light-receiving element 30b. The result of measurement is then displayed on the display panel 51. When one measurement is thus completed, the measurement value is stored in memory.

In the embodiment described above, blood-sugar value is measured. However, the test instrument of the present invention is applicable also to devices which analyze uric acid, GOT (Glutamic Oxaloacetic Transaminase), GPT (Glutamic Pyruvic Transaminase), cholesterol, etc.

Furthermore, the instrument can be applied to liquids other than blood, such as urine and saliva. In addition, the first and second openings need not be circular but can be elliptical or polygonal.

Thus, in accordance with the present invention as described above, a specimen can be distributed on the specimen regent layer uniformly and in a fixed concentration even if an excess amount of specimen attaches itself to the instrument. In addition, surplus specimen which has nowhere to travel will not drip from the test instrument.

Furthermore, the test instrument rapidly absorbs excess specimen.

Even if the specimen is not distributed uniformly over a wide area, the specimen will be distributed evenly at the opening where measurement is performed. If the user confirms merely the uniformity of color over the area of the measurement opening at the end of measurement, it is possible to judge whether the specimen has attached itself in a uniform distribution, namely whether an accurate measurement has been performed.

As many apparently widely different embodiments of the present invention can be made without departing from the spirit and scope thereof, it is to be understood that the invention is not limited to the specific embodiments thereof except as defined in the appended claims.

What is claimed is:

1. A test instrument on which a specimen is spread for being measured by a measuring device, comprising:
    a base member having a first opening for passing a specimen,
    a second opening in said base member,
    a flat specimen spreading layer obtained from flat material and having a first portion of a first surface thereof which is exposed to said first opening and a second portion of said first surface which is not exposed to said first opening,
    a flat reagent layer obtained from flat material and being in contact with a second surface of said specimen spreading layer,
    a flat light-transmissive layer obtained from flat material in contact with said reagent layer,
    said second opening provided on an opposite side of said base member than said first opening, at which second opening measurement is performed by a measuring device,
    said second opening is smaller than said first opening,
    a flat absorbing layer provided in direct contact with the second portion of the first surface of said flat specimen spreading layer in order to absorb excess specimen which has been collected on said flat specimen spreading layer while allowing said first portion to remain exposed to said first opening, thus allowing said flat specimen spreading layer to be exposed to atmosphere for quickly drying said reagent layer, and wherein an edge portion of said second opening is chamfered with a predetermined angle to allow a wider optical path transmitted from the measuring device.

2. The test instrument according to claim 1, wherein the diameter of said first opening is set to be about twice the diameter of said second opening.

3. The test instrument according to claim 2, wherein the reagent layer comprises a reagent for reacting with said specimen so that blood-sugar value can be measured by coloration of the reagent layer.

4. The test instrument according to claim 2, wherein the reagent layer comprises a reagent for reacting with said specimen so that uric acid can be measured by coloration of the reagent layer.

5. The test instrument according to claim 2, wherein the reagent layer comprises a reagent for reacting with said specimen so that Glutamic Oxaloacetic Transaminase can be measured by coloration of the reagent layer.

6. The test instrument according to claim 2, wherein the reagent layer comprises a reagent for reacting with said specimen so that Glutamic Pyruvic Transaminase can be measured by coloration of the reagent layer.

7. The test instrument according to claim 1, which further comprises a covering portion which includes said first opening, wherein the first opening in the covering portion is gradually decreasing towards said specimen spreading layer and has said absorbing layer therein.

8. The test instrument according to claim 7, wherein said inner peripheral region of said first opening is formed into a circular cone-shaped configuration having an opening area which gradually diminishes toward said specimen spreading layer.

9. The test instrument according to claim 8, wherein the reagent layer comprises a reagent for reacting with said specimen so that blood-sugar value can be measured by coloration of the reagent layer.

10. The test instrument according to claim 8, wherein the reagent layer comprises a reagent for reacting with said specimen so that uric acid can be measured by coloration of the reagent layer.

11. The test instrument according to claim 8, wherein the reagent layer comprises a reagent for reacting with said specimen so that Glutamic Oxaloacetic Transaminase can be measured by coloration of the reagent layer.

12. The test instrument according to claim 8, wherein the reagent layer comprises a reagent for reacting with said specimen so that Glutamic Pyruvic Transaminase can be measured by coloration of the reagent layer.

13. The test instrument according to 7, wherein an inner peripheral region of said first opening is formed into a circular cone-shaped configuration having an outwardly bulging curved surface and an opening area which gradually diminishes toward said specimen spreading layer.

14. The test instrument according to claim 13, wherein the reagent layer comprises a reagent for reacting with said specimen so that blood-sugar value can be measured by coloration of the reagent layer.

15. The test instrument according to claim 13, wherein the reagent layer comprises a reagent for reacting with said specimen so that uric acid can be measured by coloration of the reagent layer.

16. The test instrument according to claim 13, wherein the reagent layer comprises a reagent for reacting with said specimen so that Glutamic Oxaloacetic Transaminase can be measured by coloration of the reagent layer.

17. The test instrument according to claim 13, wherein the reagent layer comprises a reagent for reacting with said specimen so that Glutamic Pyruvic Transaminase can be measured by coloration of the reagent layer.

18. The test instrument according to claim 7, wherein the reagent layer comprises a reagent for reacting with said specimen so that blood-sugar value can be measured by coloration of the reagent layer.

19. The test instrument according to claim 7, wherein the reagent layer comprises a reagent for reacting with said specimen so that uric acid can be measured by coloration of the reagent layer.

20. The test instrument according to claim 7, wherein the reagent layer comprises a reagent for reacting with said specimen so that Glutamic Oxaloacetic Transaminase can be measured by coloration of the reagent layer.

21. The test instrument according to claim 7, wherein the reagent layer comprises a reagent for reacting with said specimen so that Glutamic Pyruvic Transaminase can be measured by coloration of the reagent layer.

22. The test instrument according to claim 1, wherein the reagent layer comprises a reagent for reacting with said specimen so that blood-sugar value can be measured by coloration of the reagent layer.

23. The test instrument according to claim 1, wherein the reagent layer comprises a reagent for reacting with said specimen so that uric acid can be measured by coloration of the reagent layer.

24. The test instrument according to claim 1, wherein the reagent layer comprises a reagent for reacting with said specimen so that Glutamic Oxaloacetic Transaminase can be measured by coloration of the reagent layer.

25. The test instrument according to claim 1, wherein the reagent layer comprises a reagent for reacting with said specimen so that Glutamic Pyruvic Transaminase can be measured by coloration of the reagent layer.

26. The test instrument according to claim 1, further comprising backward insertion preventing means on the base member for preventing the test instrument from being inserted backwardly into the measuring device.

27. The test instrument according to claim 26, wherein said backward insertion preventing means is formed near said first opening.

28. The test instrument according to claim 26, further comprising a second backward insertion preventing means mounted on the measuring device for coacting with the backward insertion preventing means on said base member.

29. The test instrument according to claim 28, wherein said second backward insertion preventing means is formed as a cut-out and said backward insertion preventing means on said base member is formed as a projection to mate with said cutout.

30. A test instrument on which a specimen is spread for being measured by a measuring device, comprising:
 a base member having a first opening for passing a specimen;
 a second opening in said base member;
 a specimen spreading layer having a first portion of a first surface thereof which is exposed to said first opening and a second portion of said first surface which is not exposed to said first opening;
 a reagent layer in contact with a second surface of said specimen spreading layer;
 a support member in contact with said reagent layer;
 said second opening provided on an opposite side of said base member than said first opening, at which second opening measurement is performed by a measuring device;
 an absorbing layer provided in direct contact with the second portion of the first surface of said specimen spreading layer in order to absorb excess specimen which has been collected on said specimen spreading layer while allowing said first portion to remain exposed to said first opening;
 wherein the diameter of said first opening is about twice the diameter of said second opening; and a covering portion of said base member which includes said first opening and which gradually extends towards said specimen spreading layer and said absorbing layer is mounted between said covering portion and the second portion of the first surface of the specimen spreading layer; and wherein an edge portion of said second opening is chamfered with a predetermined angle to allow a wider optical path transmitted from the measuring device.

31. The test instrument according to claim 30, wherein an inner peripheral region of said first opening is formed into a circular cone-shaped configuration having an opening area which gradually extends toward said specimen spreading layer.

32. The test instrument according to claim 30, wherein said absorbing layer is annular and said covering portion extends into a center part of said annular absorbing layer.

33. A test instrument on which a specimen is spread for being measured by a measuring device comprising:
a base member having a first opening for passing said specimen;
a second opening in said base member;
a specimen spreading layer having a first portion of a first surface thereof which is exposed to said first opening and a second portion of said first surface which is not exposed to said first opening;
a reagent layer in contact with a second surface of said specimen spreading layer;
a support member in contact with said reagent layer;
said second opening provided on an opposite side of said base member than said first opening, at which second opening measurement is performed by a measuring device;
said second opening is smaller than said first opening;
an absorbing layer provided in direct contact with the second portion of the first surface of said specimen spreading layer in order to absorb excess specimen which has been collected on said specimen spreading layer while allowing said first portion to remain exposed to said first opening; and
wherein an edge portion of said second opening is chamfered with a predetermined angle to allow a wider optical path transmitted from said measuring device.

34. The test instrument according to claim 33, wherein the diameter of said first opening is about twice the diameter of said second opening.

35. The test instrument according to claim 33, further comprising a covering portion of said base member which includes said first opening, wherein the first opening in the covering portion gradually extends towards said specimen spreading layer and said absorbing layer is mounted between the covering portion and the second portion of the first surface of the specimen spreading layer.

* * * * *